(12) United States Patent
Malcolm et al.

(10) Patent No.: US 10,000,730 B2
(45) Date of Patent: Jun. 19, 2018

(54) BIOMATERIAL HANDLING DEVICE

(71) Applicant: The Jackson Laboratory, Bar Harbor, ME (US)

(72) Inventors: Joan Malcolm, Bar Harbor, ME (US); Shannon Byers, Lamoine, ME (US); Robert A. Taft, Bar Harbor, ME (US); Paul C. Sabin, Needham, MA (US); Andrew David Zdeblick, Boston, MA (US); Ivan Goryachev, Nashua, NH (US)

(73) Assignee: The Jackson Laboratory, Bar Harbor, ME (US)

( * ) Notice: Subject to any disclaimer, the term of this patent is extended or adjusted under 35 U.S.C. 154(b) by 244 days.

(21) Appl. No.: 14/877,969

(22) Filed: Oct. 8, 2015

(65) Prior Publication Data

US 2016/0083680 A1 Mar. 24, 2016

Related U.S. Application Data

(63) Continuation of application No. 13/765,978, filed on Feb. 13, 2013, now abandoned.

(60) Provisional application No. 61/597,944, filed on Feb. 13, 2012.

(51) Int. Cl.
*C12M 3/00* (2006.01)
*C12M 1/00* (2006.01)
*C12M 1/04* (2006.01)
*C12M 1/12* (2006.01)

(52) U.S. Cl.
CPC ............ *C12M 21/06* (2013.01); *C12M 23/20* (2013.01); *C12M 23/24* (2013.01); *C12M 23/38* (2013.01); *C12M 37/04* (2013.01)

(58) Field of Classification Search
CPC ...... C12M 21/06; C12M 23/04; C12M 23/12; C12M 23/24; C12M 23/34; C12M 23/38; C12M 23/44; C12M 23/46; C12M 25/04; B01L 3/50853; B01L 3/50855; B01L 2300/048; G01N 2001/315
See application file for complete search history.

(56) References Cited

U.S. PATENT DOCUMENTS

| 4,877,659 A | 10/1989 | Vince |
| 5,681,746 A | 10/1997 | Brian et al. |
| 5,741,463 A | 4/1998 | Sanadi |
| 5,795,773 A | 8/1998 | Read et al. |
| 6,517,781 B1 | 2/2003 | Coassin et al. |
| 2000/3215940 | 11/2003 | Lacey et al. |
| 2004/0115798 A1 | 6/2004 | Ma et al. |
| 2007/0166816 A1 | 7/2007 | Campbell et al. |

*Primary Examiner* — William H. Beisner
(74) *Attorney, Agent, or Firm* — Ajay A. Jagtiani; Miles & Stockbridge P.C.

(57) ABSTRACT

A biomaterial handling device is described that will provide for functionality for performing both IVF procedures and washing techniques in a single device. Disclosed embodiments provide increased protection to biomaterial samples during processing and handling. Embodiments of the invention reduce labor intensive processes for both IVF and washing treatments and address reduced risks of contamination of biological samples by providing an increasingly sterile environment.

61 Claims, 11 Drawing Sheets

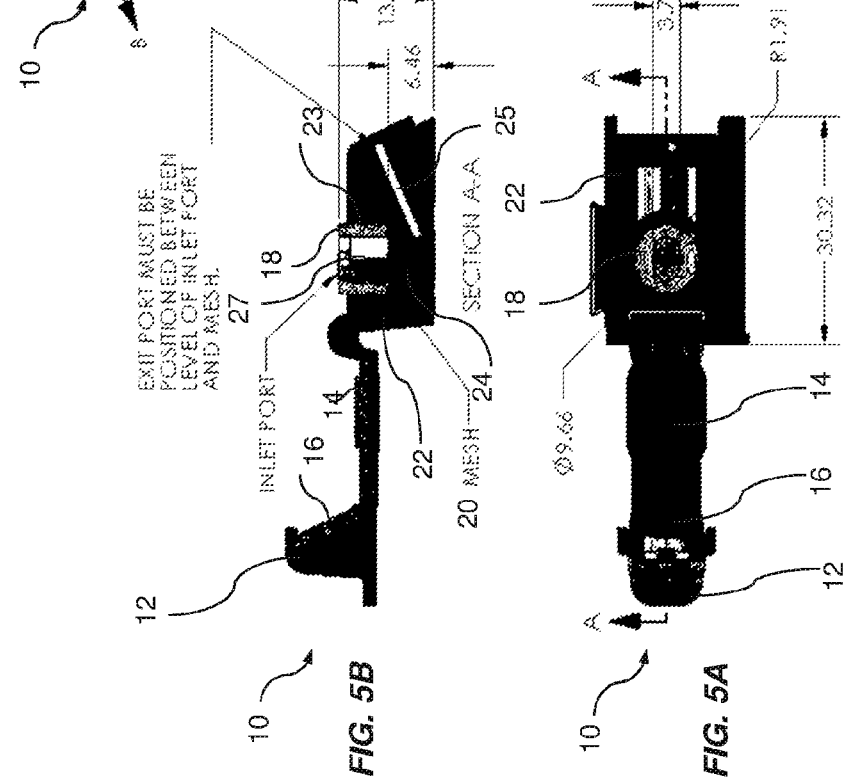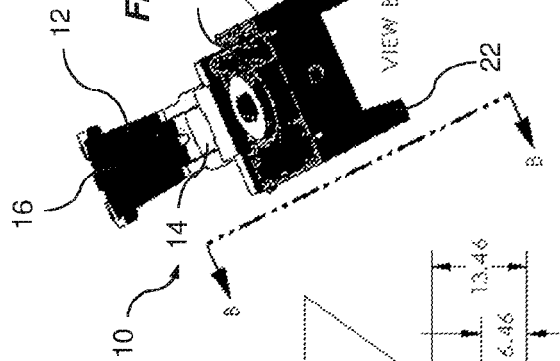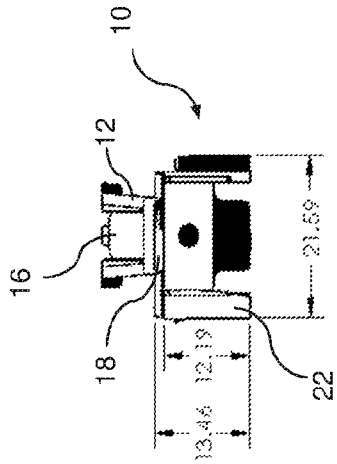

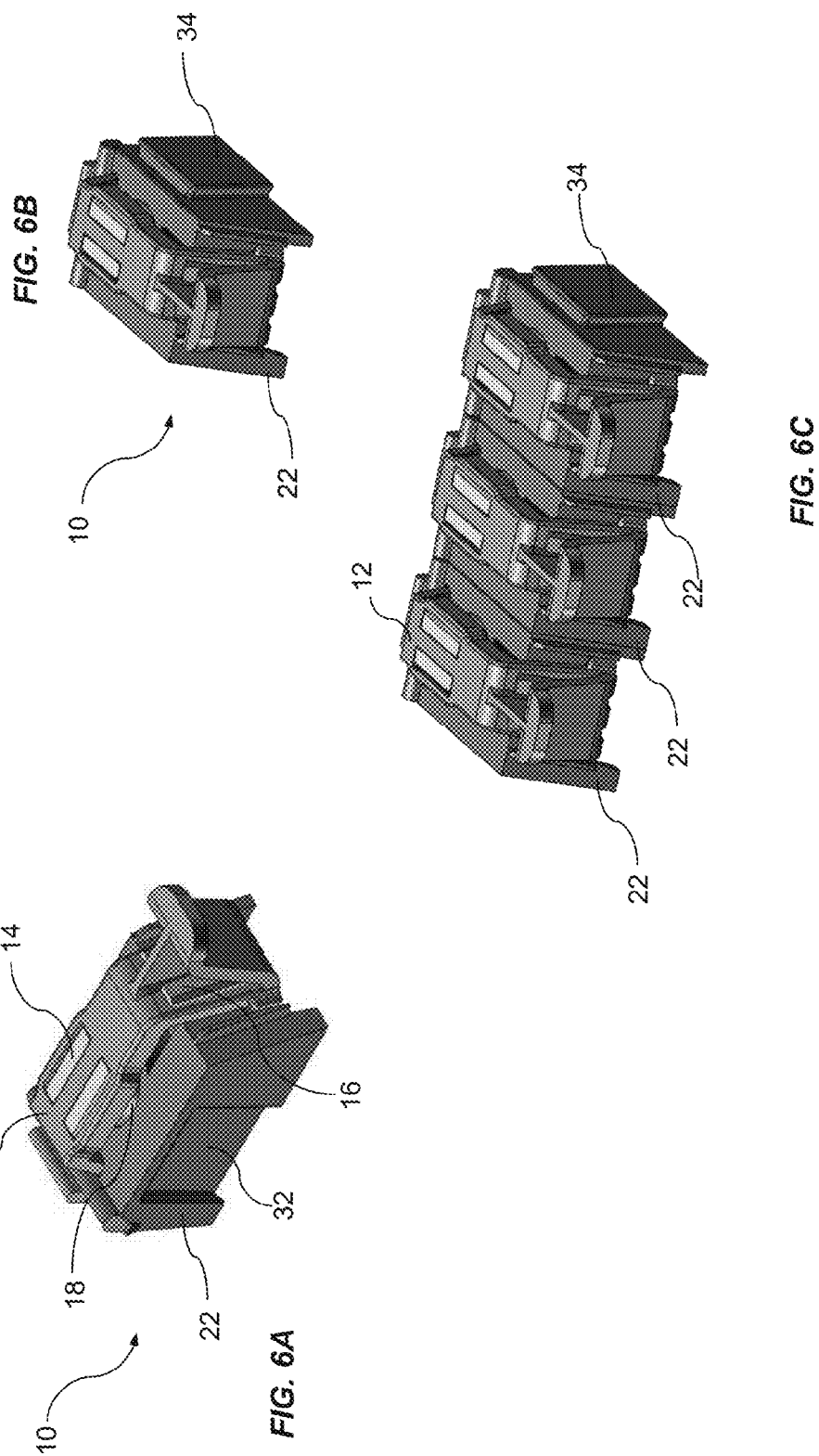

BIOMATERIAL HANDLING DEVICE

PRIORITY DATA AND INCORPORATION BY REFERENCE

This application is a continuation of U.S. patent application Ser. No. 13/765,978, filed Feb. 13, 2013, now abandoned, which claims benefit of priority to U.S. Provisional Patent Application No. 61/597,944, entitled "Biomaterial Handling Device," filed Feb. 13, 2012, which is incorporated by reference in its entirety.

BACKGROUND

Field of the Invention

The present invention generally concerns handling of embryos. More particularly, the present invention relates to an apparatus and process for performing in vitro fertilization (IVF) and washing techniques.

Related Art

Technology-assisted reproduction techniques in which embryos are handled independently from their mammalian biological source are growing in importance and frequency of use. Such techniques have great direct benefit to persons unable to have babies through unassisted sexual reproduction. In some instances, such assisted reproduction techniques are employed to control faster genetic evolution of a mammal, such as cattle or fish, and permitting the genetic characteristics of the single exceptional mammal to be passed on to far greater numbers of offspring than would be possible through unassisted sexual reproduction.

Embryo manipulation is becoming more routine due to the development of gene manipulation, cloning, and in vitro fertilization (IVF) techniques. The overall goal of embryo manipulation may be to increase production efficiency, especially with regard to reproduction, milk production or production of specific milk components, lean tissue growth with reduced fat content and decreased susceptibility to specific diseases. Embryo transfer is also used to introduce or rescue valuable germplasm and to propagate rare breeding animals such as endangered exotic species.

Expense and relatively low success rates place significant burdens on the use of these assisted reproduction techniques for humans as well as other mammals. In human reproduction, such expense and failure may add emotional as well as economic burdens. In addition, safeguards against failures often result in unwanted or unmanageable multiple births, as well as additional stored embryos which may require maintenance and additional difficult decision making at some later point in time. Expense is generally a primary concern, for example, in animal reproduction.

Failure rates in reproduction techniques as well as testing and other embryo handling techniques are attributable primarily to the significant handling and manipulation of embryos in executing these techniques. Animal reproductive technologies have advanced in recent years, but the physical tools used in animal reproduction have not changed significantly. Fine-bore glass pipettes are still one of the basic tools of the embryologist. Using standard petri dishes, procedures such as in vitro maturation of eggs (IVM), in vitro fertilization (IVF) and embryo culture (EC) require picking up and placing individual eggs and embryos several times for each procedure.

Such handling and movement from one petri dish to another provides significant potential for damage or contamination. Perhaps more important, though, is the failure of a stationary embryo in a petri dish to simulate the corresponding natural biological reproduction condition. Some efforts have been made to move embryos in petri dishes via agitation of the dish, but this is a haphazard approach. Expense is also created here due to the relatively large amount of biological medium required for the manual petri dish conventional embryo handling methods. Bovine embryos are individually handled with pipettes and large, expensive manipulators. Large quantities of biological medium, including growth agents for human embryo culturing, renders the corresponding in vitro procedure even more expensive.

Such static culture systems also fail to allow for changing the milieu in the culture medium as the embryo develops. Current culture systems with flowing medium have limited volumetric culture chambers. However, a concern exists if the culture volumes are greater than needed and medium is replenished too quickly. The endogenous growth factors that enhance development may be diluted out and washed away.

Furthermore, a concern also exists during manual techniques for washing embryos to reduce rates of pathogen transmissions employed in washing steps (e.g., typical washing steps may include ten washes per embryo). Typical prior-art systems require a laborer to manually monitor and manipulate embryos from one media to another during washing procedures. This method is not only labor and time intensive, but, may also subject the embryos to contaminants during treatment. In addition, once IVF and washing techniques are complete, it may be further necessary to treat the embryos in another remote facility. Conventional systems require the embryos to be manually placed in shipping containers for transport. Again, this potentially places the embryos at risk by exposing them to contaminants or other risks during passage. The same is true when the embryos arrive at the remote location and need to be handled for further treatment and/or manipulation.

Thus, there is a need for an improved embryo handling device and method which addresses problems in known embryo handling techniques. An improved embryo handling device and method should provide for an improved simulation of natural conditions. It should also provide a building block upon which larger and/or more powerful and accurate instruments may be based, such as embryo culturing systems, embryo analysis systems, embryo storage systems and similar systems.

SUMMARY OF THE INVENTION

It is, therefore, an object of the present invention to overcome the deficiencies of the prior art to include a biomaterial handling device that will provide for functionality for performing both IVF procedures and washing techniques in a single device. It is a further goal of the disclosed embodiments to provide increased protection to biomaterial samples during processing and handling. Embodiments of the invention reduce labor intensive processes for IVF and washing treatments and address reduced risks of contamination of biological samples by providing an increasingly sterile environment.

In accordance with a disclosed exemplary embodiment, a biomaterial handling device is provided that, in at least some aspects of the invention, comprises a main body portion including an internal receptacle, a waste chamber connected to the internal receptacle and at least one output port connected to the waste chamber. An insert may be provided having an inlet port opening at one end of the insert and a wash chamber, wherein the inlet port opening allows access to the wash chamber disposed within an interior of the insert.

The wash chamber terminates into an opening at a bottom end of the insert; the insert further comprises a sealing ring around an exterior circumference of the insert. The biomaterial handling device may also comprise a removably attached lid connected to the main body portion for sealing the inlet port opening and the output port.

In accordance with another embodiment of the present invention, an apparatus is provided for performing an IVF procedure and washing technique. The apparatus comprises a main body portion including an internal receptacle configured to perform the IVF procedure therein. A waste chamber is connected to the internal receptacle and an output port is connected to the waste chamber. The output port terminates in an output port opening, wherein the output port extends from the waste chamber such that the output port opening is fixed at a height between an opening of the internal receptacle and the connection of the waste chamber to the receptacle. The main body portion is configured to receive media into the internal receptacle, through the waste chamber and output port, and out of the output port opening to perform the washing technique.

In yet another embodiment of the present invention, an apparatus is provided for performing an IVF procedure and washing technique. The apparatus comprises a main body portion including an internal receptacle configured to perform the IVF procedure therein. A waste chamber is connected to an opening of the internal receptacle and an output port is connected to the waste chamber. The output port terminates in an output port opening, wherein the output port extends from the waste chamber such that the output port opening is fixed at a height between an opening of the internal receptacle and the connection of the waste chamber to the receptacle. The main body portion is configured to receive media into the internal receptacle, through the waste chamber and output port, and out of the output port opening to perform the washing technique.

There has thus been outlined, rather broadly, certain embodiments of the invention in order that the detailed description of the invention herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the concept upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The accompanying drawings, which are incorporated herein and constitute part of this specification, illustrate exemplary embodiments of the invention and, together with the detailed description given below, serve to explain the features of the invention.

FIG. 5A illustrates a top view of the biomaterial handling device of FIG. 1 in an open configuration in accordance with an embodiment of the invention;

FIG. 5B illustrates a cross-sectional view of the biomaterial handling device taken along line A-A of FIG. 5A in accordance with an embodiment of the invention;

FIG. 5C illustrates a view of the biomaterial handling device taken along line B-B of FIG. 5B in accordance with an embodiment of the invention;

FIG. 5D illustrates a frontal view of the biomaterial handling device of FIG. 5A in accordance with an embodiment of the invention;

FIGS. 6A-6C illustrate the interlocking feature of the biomaterial handling device for assembling an array of devices in accordance with an embodiment of the invention.

DETAILED DESCRIPTION OF THE PREFERRED EMBODIMENTS

Definitions

Figure 1:
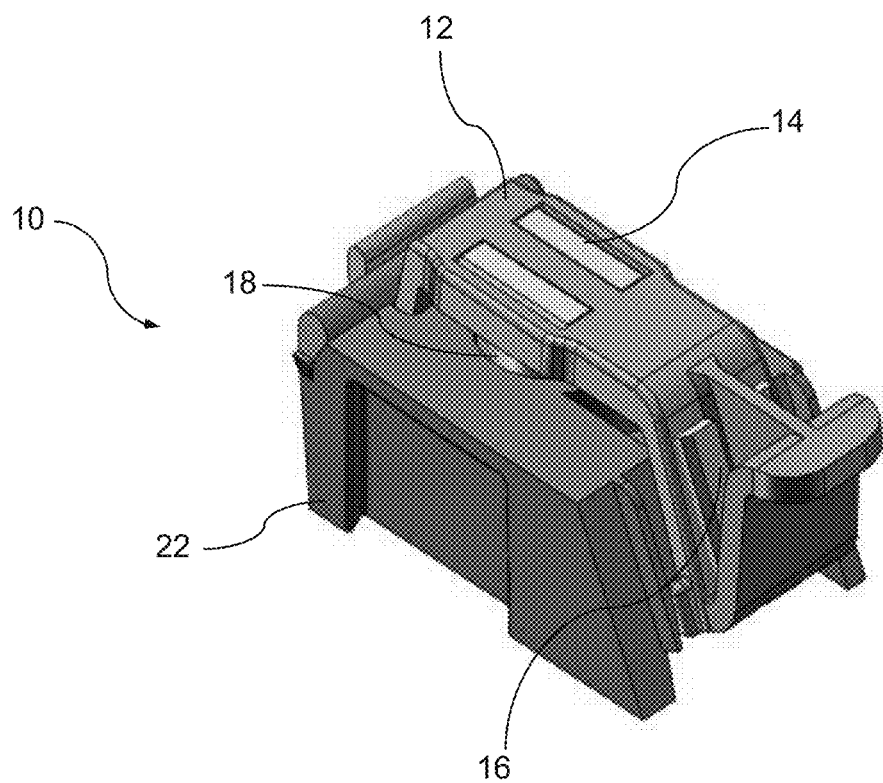
FIG. 1 illustrates a perspective view of the example biomaterial handling device constructed in accordance with an embodiment of the invention.

Where the definition of a term departs from the commonly used meaning of the term, applicant intends to utilize the definitions provided below, unless specifically indicated.

For the purposes of the present invention, the term an "agar" is meant to refer to a gel made from red algae that is used to culture certain disease agents in the laboratory. As a gel, an agarose medium is porous.

For the purposes of the present invention, the term an "array" is meant to refer to a systematic arrangement of objects, usually in rows and/or in columns.

For the purposes of the present invention, the term "biomaterial handling device" is used to describe the entire general embodiment of the invention article.

For the purposes of the present invention, the term "in vitro fertilization" (IVF) is a process by which egg cells are fertilized by sperm outside the body.

For the purposes of the present invention, the terms "media" or "wash media" is meant as a general reference to describe any liquid (typically buffered salt solutions) to which gametes or embryos may be exposed including, for example, Human Tubal Fluid (HTF) or other media capable of supporting fertilization in vitro.

For the purposes of the present invention, the term "permeability" is used to describe a measure of the ability of a substance (such as a porous material) to allow another substance (such as a gas or fluid) to pass through it.

DESCRIPTION

The invention will now be described with reference to the drawing figures, in which like reference numerals refer to like parts throughout. The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Turning to FIG. 1, the present invention consists of a biomaterial handling device 10 configured and suitable to perform in vitro fertilization procedures and washing techniques within the device. The biomaterial handling device 10 consists of a main body portion 22 and is suitably configured to receive additional components to its external structure and throughout its internal structure. The material of main body portion 22 includes polystyrene or other suitable material for performing in vitro fertilization procedures and washing techniques. The material of main body portion 22 is also suitable for withstanding sterilization processes as outlined below.

A lid 12 is affixed to main body portion 22. Lid 12 is configured to receive a plurality of seals 14, 16 for sealing biomaterial specimens within main body portion 22. The material of lid 12 may also include polystyrene, polypropylene, hi-density polyethylene, McMaster 9218T82, Sefar 07-57/24, Sefar 07/51/33, or other suitable material for performing in vitro fertilization procedures and washing techniques. The material of lid 12 is also suitable for withstanding sterilization processes as outlined below.

Figure 2:
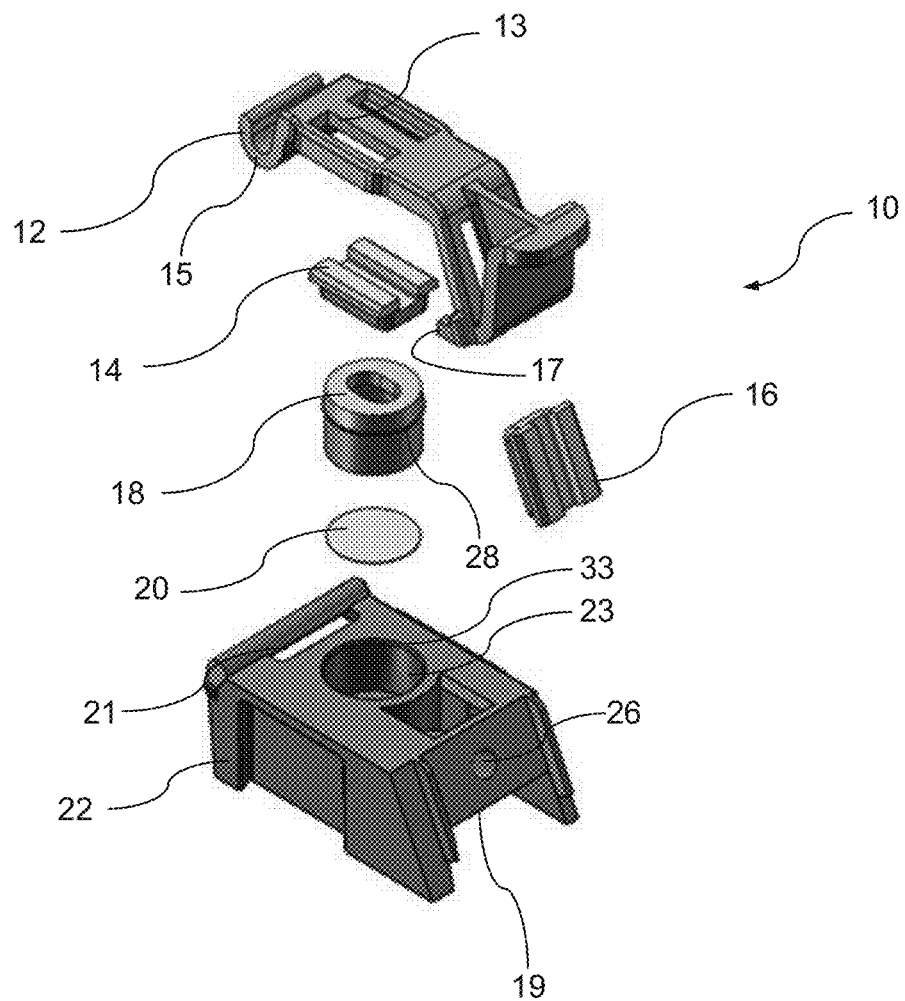
FIG. 2 illustrates an exploded view of the biomaterial handling device of FIG. 1 in accordance with an embodiment of the invention.

Turning to the exploded view of FIG. 2, an arrangement of lid 12 is designed to receive seals 14, 16 via receptacle portions 13 for receiving corresponding mating portions of seals 14, 16 disposed therein. Each of seals 14, 16 may simply be snap-fitted into receptacle portions 13. Embodiments for seals 14, 16 provide certain elasticity for sealing lid 12 against portions of main body portion 22. While the aforementioned description is provided for outlining an embodiment for retaining seals 14, 16 to lid 12, other suitable means for retaining seals 14, 16 at disposed locations on lid 12 may be employed. The material of seals 14, 16 may include a thermoplastic elastomer, silicone or other suitable materials for sealing internal components of device 10, including being suitable for withstanding sterilization processes as outlined below. Since liquid media will be introduced within device 10 for the purpose of, inter alia, maintaining pH levels of samples disposed therein, seals 14, 16 are sufficiently employed to seal against openings of biomaterial handling device 10 for the purpose of maintaining the aforementioned pH levels.

Disclosed embodiments of lid 12 include a hinge portion 15 for mating with a hinge receiving portion 21 of main body portion 22. The hinge portion 15 allows for rotational movement of lid 12, thereby permitting lid 12 to assume an open (e.g., see FIG. 4) and closed position (e.g., see FIG. 3) relative to main body portion 22. In a closed position, a flanged lip portion 17 of lid 12 engages a locking portion 19 of main body portion 22 in a snap-fitted arrangement, thereby locking lid 12 to main body portion 22. Once lid 12 is locked into place against main body portion 22, seals 14, 16 seal respective openings along main body portion 22, as discussed below.

Main body portion 22 is configured to receive additional components via an internal receptacle 23. Internal receptacle 23 receives an insert 18 and a filter 20 within its cavity through the opening 33 of internal receptacle 23. Thus, insert 18 and filter 20 is preferably positioned within the cavity of internal receptacle 23 and seated therein, as further described below. The material of insert 18 includes polystyrene, polypropylene, hi-density polyethylene or other suitable material for performing in vitro fertilization procedures and washing techniques. The material of insert 18 is also suitable for withstanding sterilization processes as outlined below. Filter 20 may comprise a mesh filter suitably sized with porous holes so that cumulus cells and sperm may be washed or separated through the mesh while also retaining eggs or embryos. Filter 20 may be disposed at a bottom opening of insert 18 in order to prevent leakage and facilitate assembly of biomaterial handling device 10. In some disclosed embodiments, filter 20 may be physically attached to bottom opening of insert 18 by an ultrasonically welded bond. In an alternative embodiment, filter 20 may be thermally welded to the bottom of insert 18.

Figure 3:
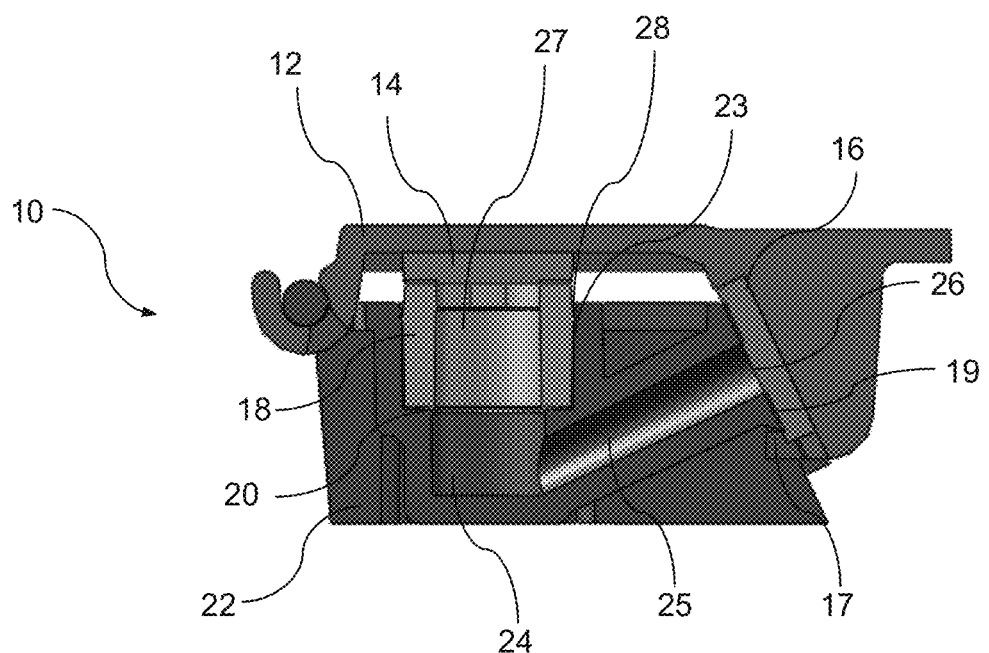
FIG. 3 illustrates an internal side view of the biomaterial handling device of FIG. 1 in a closed configuration in accordance with an embodiment of the invention.

In disclosed embodiments, the hole size for the mesh filter 20 may range from approximately 30-70 microns which is sufficiently sized to accommodate embryos for all mammals subject to IVF procedures and washing techniques. In a disclosed embodiment, a material of the mesh filter 20 may include one of polyester, nylon, polystyrene, glass, high-density polyethylene (HDPE), polypropylene, and paper. It is readily appreciated that for a variety of species, the hole size of the mesh filter 20 may be appropriately selected to prevent eggs or embryos from passing through into the waste chamber 24 (FIG. 3). Additional filters 20, for instance, having different hole dimensions, may be utilized to support IVF procedures and washing techniques for other species, including, for example, fish, amphibians and insects. For fish, the hole size for mesh filter 20 may range from approximately 50-350 microns to accommodate embryos subject to IVF procedures and washing techniques. For amphibians, the hole size for mesh filter 20 may range from approximately 50-500 microns to accommodate embryos subject to IVF procedures and washing techniques. For insects, the hole size for mesh filter 20 may range from approximately 50-150 microns to accommodate embryos subject to IVF procedures and washing techniques.

Figure 4:
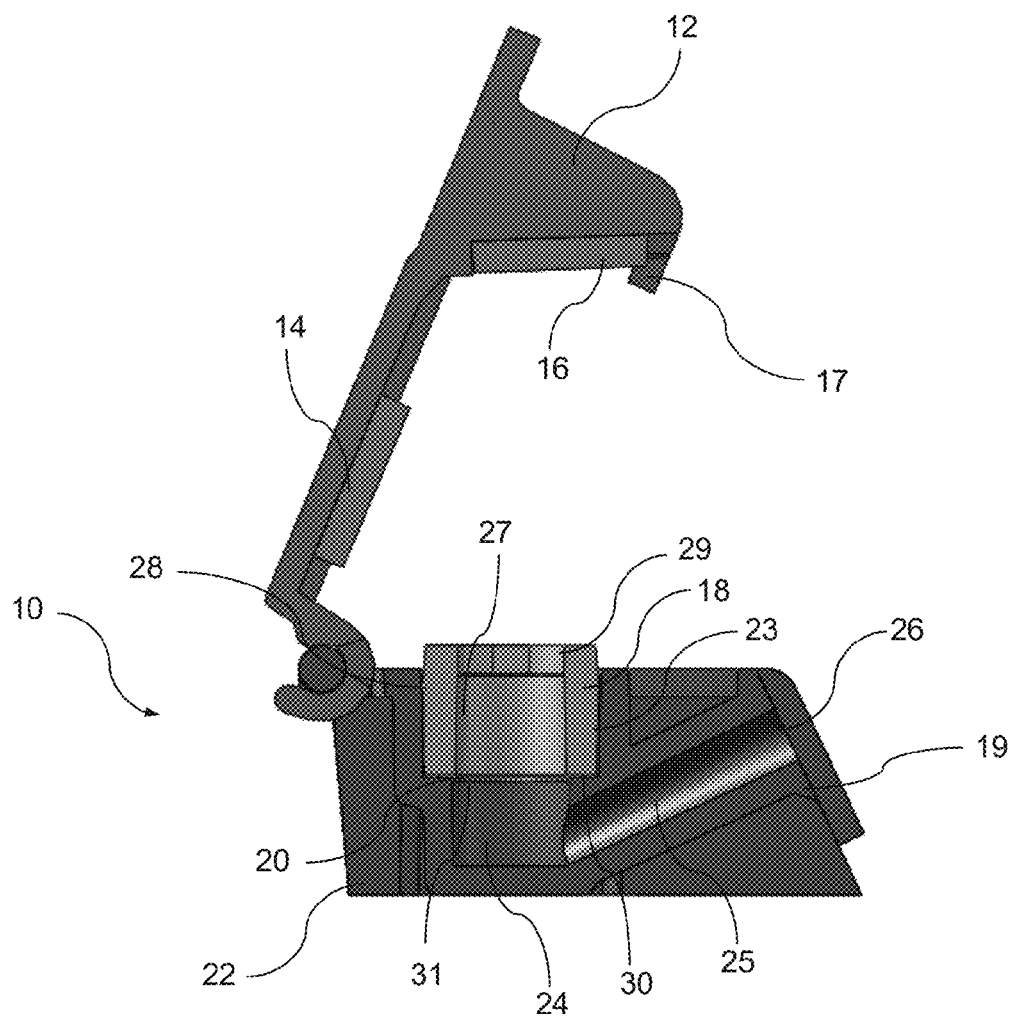
FIG. 4 illustrates the internal side view of the biomaterial handling device of FIG. 3 in an open configuration in accordance with an embodiment of the invention.

Turning to FIGS. 3 and 4, waste chamber 24 is connected to internal receptacle 23 within the interior of biomaterial handling device 10. An output port 25 having an output port opening 26 is connected to waste chamber 24, such that a unidirectional fluid flow through receptacle 23 into waste chamber 24 is configured to exit through output port 25 and out of output port opening 26. While the present embodiment illustrates one output port 25, it is conceivable to provide more than one output port 25 connected to waste chamber 24 to allow fluid flow through receptacle 23 to an exit thereof. In disclosed embodiments, output port 25 may extend from waste chamber 24 and terminate at output port opening 26. In the disclosed embodiment, the width of insert 18 is in close-fit arrangement with the diameter of internal receptacle 23. In addition, insert 18 may include a lip 28 around the circumference for sealing insert 18 within internal receptacle 23, as described below. In the disclosed embodiment, the diameter of filter 20 is also in close-fit arrangement with the diameter of internal receptacle 23. The diameter of waste chamber 24 is smaller than the diameter of internal receptacle 23. In an assembled arrangement, the increased diameter of the internal receptacle 23 provides a flanged area 30 upon which filter 20 and insert 18 are seated on top thereof.

Insert 18 comprises a top opening, a bottom opening, and an internal wash chamber 27 disposed within an interior of insert 18. Access to internal wash chamber 27 occurs through the top opening which is configured as inlet port opening 29 at one end of insert 18. Thus, specimens and media may be received through inlet port opening 29 into internal wash chamber 27 and out of insert 18 via the bottom opening. In disclosed embodiments, internal wash chamber 27 may terminate at the bottom opening. Inlet port opening 29 is substantially oval or another shape, i.e., other than round so that when a pipette is inserted within inlet port opening 29, the opening does not conform to the same shape of the pipette; thus, the pipette is incapable of forming a seal with the opening. Accordingly, the disclosed embodiment provides the capability for evacuating air from insert 18 in order to decrease any internal pressure to reduce or eliminate a possibility for damaging embryos employed during IVF and washing procedures by providing the general oval shape of inlet port opening 29. If inlet port opening 29 was similar in round shape as that of the pipette, a seal might be established which could create a pressure inside wash chamber 27. This pressure could potentially damage embryos, disposed within wash chamber 27, as media is injected via the pipette. The pressure could also create a fast flow of media through mesh 20 which could force embryos through mesh 20 causing them to be lost or damaged. Insert 18 has an opening 31 at the other end in order to allow media to flow through wash chamber 27 into waste chamber 24.

Biomaterial handling device 10 is designed to allow IVF procedures to occur, for example, within wash chamber 27. Disclosed embodiments provide the addition of sperm and eggs through inlet port opening 29. The concentration of sperm may be selected to increase the probability of the egg and sperm coming into contact. As the procedure to fertilize one or more eggs within wash chamber 27 occurs, some sperm may fall through filter 20 towards and into waste chamber 24. The distance from the position of filter 20 to the bottom of waste chamber 24 may be sufficiently designed to facilitate the efforts of sperm to swim back to one or more eggs placed within wash chamber 27, as needed. Thus, the aforementioned distance should not be so great as to impede or make the sperm struggle back up to one or more eggs disposed in wash chamber 27.

Biomaterial handling device 10 is also configured to allow washing techniques directly throughout the device. Advantages of the disclosed embodiments provide the placement of output port opening 26 at a sufficient height above the level of assembled filter 20 in a final assembly. Thus, as media is introduced and flows through inlet port opening 29, wash chamber 27, waste chamber 24 and output port 23 and out of output port opening 26, the level of media introduced into biomaterial handling device 10 will never fall below the level of filter 20 in a final assembly state. This, in turn, will prevent media from completely running out of device 10 and allowing the eggs/embryos to dry out. The height of output port opening 26 is preferably designed such that as media is introduced into the top of wash chamber 27 and flows through device 10, the media is allowed to drip out of output port opening 26 while still maintaining media volume in wash chamber 27. Thus, an important aspect of the disclosed device 10 ensures that there will always be media in the wash chamber 27 to keep the material eggs/embryos wet. Otherwise, if the height of output port opening 26 is set too low, then too much media is capable of running out of device 10 and below the level of wash chamber 27, thereby allowing the eggs/embryos to dry out. If the height of output port opening 26 is set too high, then the media will overflow from the top of wash chamber 27, which is contrary to an egg/embryo washing technique. In a preferred embodiment, biomaterial handling device 10 is designed such that the level of media introduced into biomaterial handling device 10 will always stay above filter 20. Specifically, the surface tension created at inlet port opening 29 ensures the level of the media volume at the top of insert 18 is relatively uniform. As media is added to inlet port opening 29, the top surface of the media arches upwardly until there is enough pressure to force a droplet out of outlet port opening 26. When the droplet exits out of outlet port opening 26, the top surface of the media arches inwardly and ready for more media to be added.

FIGS. 5A-5D provide an example of the dimensions for biomaterial handling device 10 including an embodiment of the positions of, at least, wash chamber 27, filter 20, waste chamber 24 and waste port opening 26 relative to one another. The dimensions (represented in millimeters) are exemplary. It is readily appreciated, by those skilled in the art, that the dimensions of device 10 may be adjusted to accommodate various sizes while maintaining the positional relationships between, at least, wash chamber 27, filter 20, waste chamber 24 and waste port opening 26, relative to one another, in order to maintain sufficient media within wash chamber 27 and to prevent overflow from the top of wash chamber 27.

In general, the volume of media required in wash chamber 27 will drive/determine the overall dimensions of biomaterial handling device 10. Other factors which may influence the overall dimensions may include, but not be limited to: the determination of a prescribed volume of media necessary to perform IVF; the determination of what volume of media in which an applied amount of sperm becomes too diluted; the scale of the device relative to the number and types of eggs utilized; and associated costs of media necessary for performing washing techniques. In a final determination, the positioning of output port opening 26 is between the level of inlet port opening 29 and filter 20. An optimal position of output port opening 26 may also be dependent on material hydrophilicity, surface tension of the liquid media and geometry of output port opening 26.

Turning to FIGS. 6A-6C, disclosed embodiments of individual biomaterial handling device 10 members are shown in connection with one another to form an array of biomaterial handling devices 10 (e.g., see FIG. 6C). This feature allows biomaterial handling devices 10 to be grouped together, for example, if similar tests or operations are performed for an array of biomaterial handling devices 10 or to keep a batch of embryos together. The array of biomaterial handling devices 10 may also be more easily handled, processed and/or transported if, again, similar tests or operations are performed for a cluster of devices 10 or if the devices need to be transported to another prescribed location. To provide the connection between biomaterial handling device 10 members, disclosed embodiments may include a key slot 32 formed on one side of biomaterial handling device 10. The key slot 32 may be formed as a depression and is regarded as a receiving portion or female member for interacting with a corresponding male portion. A key 34 may be formed on an opposite side of biomaterial handling device 10 as a protrusion or bump-out portion from the surface of biomaterial handling device 10. Key 34 is regarded as an attaching portion or male member and is sufficiently sized to correspond in mating fashion with key slot 32. In a disclosed embodiment, key 34 may interlock with key slot 32 by snap fit. In another embodiment, key 34 may be designed to slide into key slot 32. Whatever method is utilized to connect multiple biomaterial handling devices 10 together, a sufficient interference fit is provided to retain and maintain the devices 10 securely together for processing and handling. Such interference fit may also be reversed by utilizing sufficient force to undo the connection.

Prior to original use, biomaterial handling device 10 may come in two separate assemblies. The first assembly my comprise insert 18, filter 20 and main body portion 22. The second assembly may comprise lid 12 and seals 14, 16. The first and second assemblies may be sterilized independently and fitted together at a preferably sterile location, for example, by snapping lid 12 on main body portion 22.

In a final and closed assembly containing biomaterial sample(s), a single biomaterial handling device 10 (e.g., see FIG. 1) or an array of biomaterial handling devices 10 (e.g., see FIG. 6C) are sufficiently sealed via lid 12 and seals 14, 16 in connection with main body portion 22. Thus, any embryos and media disposed with one or more closed biomaterial handling devices 10 are protected from contaminants and protectively sealed, for example, to prevent exposure to the atmosphere or to withstand the rigors of transport to one or more remote locations. In addition, it may be necessary to decontaminate the outside of biomaterial handling device 10 after handling and/or transport of the device. In conventional systems, such as use with petri dishes, the procedure would typically require removal of all embryos into another storage system, enactment of decontamination procedures and reapplication of embryos for subsequent treatments. Hence, conventional methods tend to be more labor intensive and cost prohibitive. However, in accordance with the presently disclosed embodiments, the entire one or more biomaterial handling device(s) 10 may be sanitized or disinfected in the closed configuration without compromising the integrity of the biomaterial sample(s). This feature allows greater flexibility in handling and treating samples with the disclosed biomaterial handling device 10.

For example, should additional treatments require handling and transport of one or more biomaterial handling devices 10 to a remote site, the biomaterial samples are easily secured and transported within self-contained biomaterial handling device 10. Once the samples arrive at the prescribed location for subsequent treatments, they remain protected from sterilizing procedures applied to the exterior of biomaterial handling device 10. In one disclosed embodiment, the entire biomaterial handling device 10 is dipped into a liquid disinfectant (e.g., sterilizing agent) to sterilize the exterior of the device 10. Seals 14, 16 effectively seal inlet port opening 29 and output port opening 26, respectively. In addition, lip 28 acts as a sealing ring to provide a compression seal to prevent exposure to internal receptacle 23. Once properly sterilized, the liquid disinfectant or sterilizing agent is rinsed from biomaterial handling device 10, whereupon biomaterial handling device 10 is easily opened to expose respective biomaterial samples for subsequent treatments under sanitary conditions. Such sanitary conditions are necessary for maintaining the integrity and quality of the biomaterial samples.

In operation, biomaterial handling devices 10 may be prepared by inspecting each device 10 and ensuring that the insert 18 is properly disposed within internal receptacle 23. The proper placement of the filter 20 may be verified by inspection via a microscope. Each biomaterial handling device 10 may be labeled for identification. Multiple biomaterial handling devices 10 may be connected together in an array for similar testing techniques, as necessary. Once connected, the biomaterial handling devices 10 may be placed in an incubator the night before or the morning of a prescribed IVF treatment. During the morning of performing an IVF procedure, approximately 400 µl of media is added to each biomaterial handling device 10. A pipette tip is inserted through the inlet port opening 29 all the way to the filter 20, upon which, the media is expelled. Caution is exercised so as not to tip the biomaterial handling devices 10; otherwise, media may leak out of the output port opening. If the biomaterial handling devices 10 and media were at room temperature or colder, wait 30 minutes before continuing. If the biomaterial handling devices 10 and media were pre-warmed, wait 10 minutes before continuing by adding sperm.

To perform IVF with biomaterial handling device 10, approximately 8 ul of fresh sperm is added to each washer. Caution is taken to wipe any residual oil from the pipette tip prior to adding sperm to biomaterial handling device 10. Clutches are added to each biomaterial handling device 10. An estimate of the number of eggs added to biomaterial handling device 10 is taken and noted. This estimate may be used to check if one is able to retrieve the same number of eggs from the respective biomaterial handling device 10. Wait 30 minutes after the IVF procedure and secure lid 12 to body 22 of biomaterial handling device 10.

To perform a washing procedure, the media is preferably warmed to approximately 37 degrees C. Biomaterial handling device 10 is removed from an incubator and held over a petri dish. Approximately 500 µl of media is introduced into biomaterial handling device 10 via pipette. The flow rate of the media may be monitored to ensure that too much flow does not cause media to overflow out of inlet port opening 29. If the flow rate is too much, this may also cause embryos to pass through or to become lodged in filter 20. If the flow rate is too slow, an overly slow flow rate will waste time and unnecessarily expose the media to the atmosphere. This may possibly cause a temperature shock to the embryos, for example, while the incubator is open during the wash procedure. Any waste received from biomaterial handling device 10 (e.g., via output port opening 26) may be inspected to see if there are any eggs.

To remove the embryos from biomaterial handling device 10, one may pick up approximately 500 µl of media using a wide bore 1000 µl tip pipette. A step (A) may be performed by: adding approximately 100-150 µl of media into the washer. Adding media will cause the embryos to float off filter 20. A step (B) may be performed by: using a pipette to draw approximately 100-150 µl of media out of the washer and into a petri dish. Repeat steps (A) and (B) approximately three or four times. Count the embryos. Refer back to the earlier estimate made when adding clutches. If the number of embryos is close to the estimate, the procedure may be terminated. If not, the entire procedure for removing embryos may be repeated until more embryos are removed from biomaterial handling device 10.

Some standard IVF procedures use drops of media that are placed under a bather in order to limit evaporation of the media. In some examples, a layer of mineral oil is placed over the media, such as, in a petri dish. The petri dish is kept in an incubator and covered with a 5% $CO_2$, 5% $O_2$, 90% $N_2$ gas mixture. The mineral oil is $CO_2$ permeable. There are buffers in the media to maintain pH that require $CO_2$ to be effective. Without $CO_2$, the pH may drift and, hence, lower the embryo yield.

The applied usage of such standard IVF procedures, including the use of typical equipment, such as petri dishes still provide significant potential for damage and/or contamination in addition to the other challenges described earlier above. In an effort to address the described need, embodiments of the present invention provide a biomaterial handling device 10 which may be formed (e.g., injection molded) out of a gas permeable moisture barrier such as a $CO_2$ permeable material. The $CO_2$ permeable material may include, for example, polymethylpentene (PMP), silicone or low density polyethylene (LDPE). Thus, in some preferred embodiments, the plastic of the disclosed biomaterial handling device 10 may include material having a high $CO_2$ permeability and low water permeability.

Figure 8:
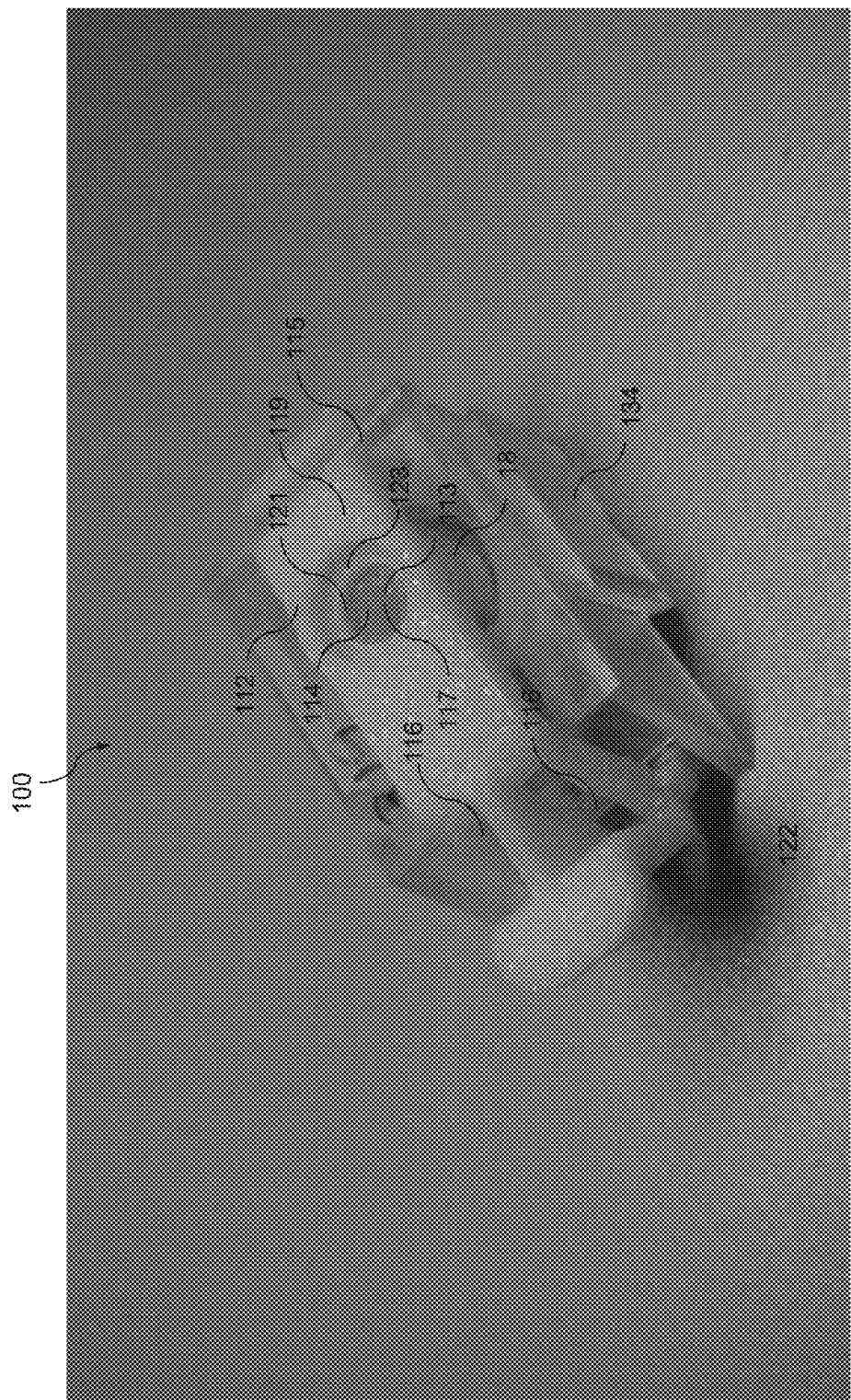
FIG. 8 illustrates a perspective view of an another embodiment of a biomaterial handling device having an alternate lid and sealing configuration.
Figure 9:
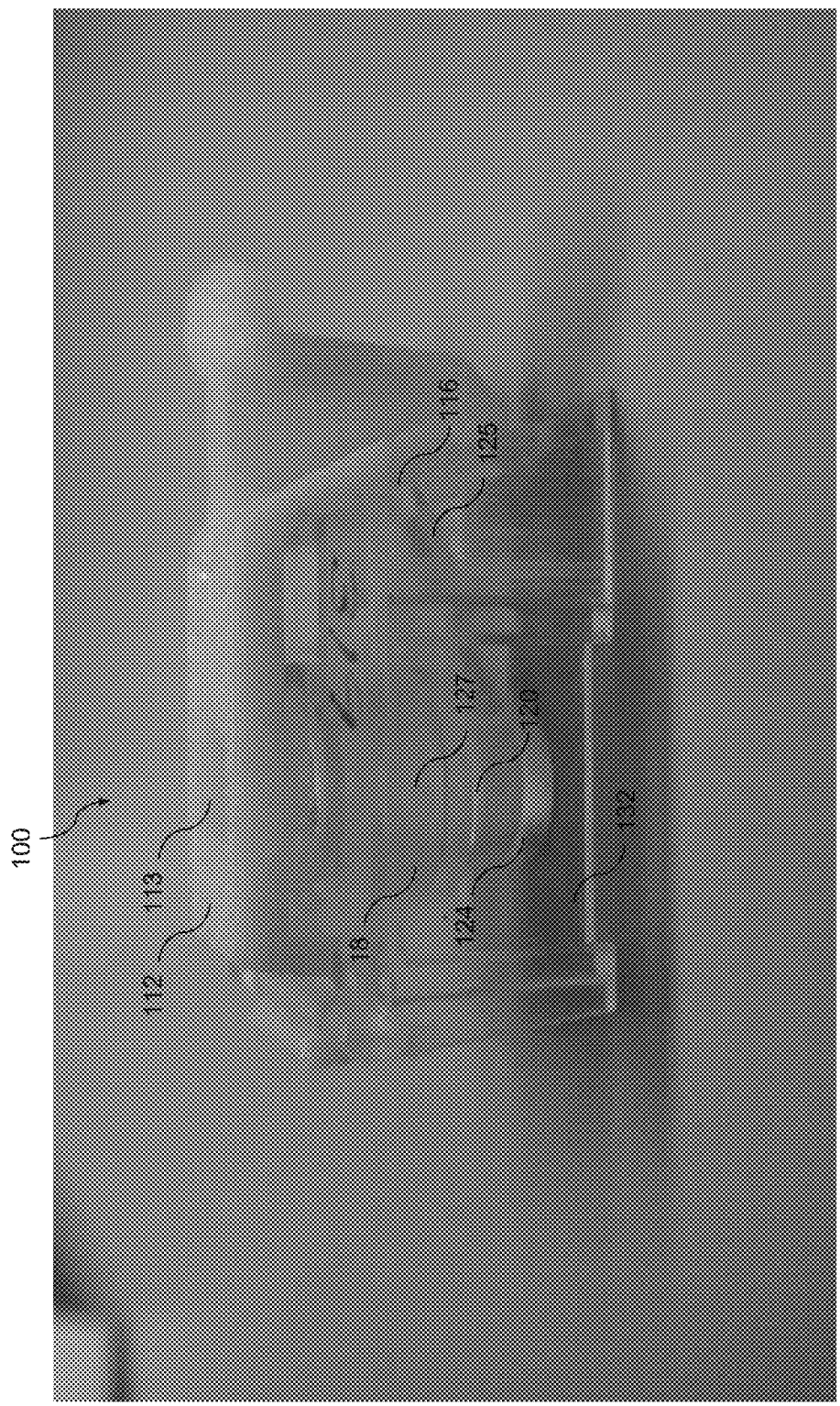
FIG. 9 illustrates an internal side view of the biomaterial handling device of FIG. 8 in a closed configuration in accordance with an embodiment of the invention.

Turning to FIGS. 8 and 9, another embodiment of the present invention consists of a biomaterial handling device 100 configured and suitable to perform in vitro fertilization procedures and washing techniques within the device. The biomaterial handling device 100 is configured and constructed in many of the same ways as the previously described biomaterial handling device 10. For example, biomaterial handling device 100 consists of a main body portion 122 and is suitably configured to receive additional components to its external structure and throughout its internal structure. The material of main body portion 122 may include polystyrene or other suitable material for performing in vitro fertilization procedures and washing techniques. The material of main body portion 122 is also suitable for withstanding sterilization processes as outlined below. Thus the particulars of main body portion 122 and the internal structure within main body portion 122 is substantially the same as that of main body portion 22 and its respective internal structure of biomaterial handling device 10. Likewise, the same components (such as insert 18) may be received within and utilized by the internal structure of main body portion 122. Accordingly, the biomaterial handling device 100 may operate similarly as the previously described biomaterial handling device 10. This embodiment of biomaterial handling device 100 may also be constructed out of a material, such as plastic having high $CO_2$ permeability and low water permeability.

Furthermore similar external elements of main body portion 22 may be employed in and on main body portion 122 including, for example, the ability/feature to cluster together one or more biomaterial handling devices 100. Accordingly, to provide a connection between biomaterial handling device 100 members, disclosed embodiments may include a key slot 132 formed on one side of biomaterial handling device 100. The key slot 132 may be formed as a depression and is regarded as a receiving portion or female member for interacting with a corresponding male portion. A key 134 formed on an opposite side of biomaterial handling device 100 as a protrusion or bump-out portion from the surface of biomaterial handling device 100. Key 134 is regarded as an attaching portion or male member and is sufficiently sized to correspond in mating fashion with key slot 132. Key 134 may interlock with key slot 132 by snap fit. In another embodiment, key 134 may be designed to slide into key slot 132. Whatever method is utilized to connect multiple biomaterial handling devices 100 together, a sufficient interference fit is provided to retain and maintain the devices 100 securely together for processing and handling in a similar manner and fashion as described with respect to multiple biomaterial handling devices 10. Such interference fit may also be reversed by utilizing sufficient force to undo the connection.

A lid 112 may be affixed to main body portion 122 in a similar arrangement as described for biomaterial handling device 10 above. Lid 112 is configured to receive a plurality of seals 116, 117 for sealing biomaterial specimens within main body portion 122. The material of lid 112 may also include polystyrene, polypropylene, hi-density polyethylene or other suitable material for performing in vitro fertilization procedures and washing techniques. The material of lid 12 is also suitable for withstanding sterilization processes as outlined below.

Figure 10:
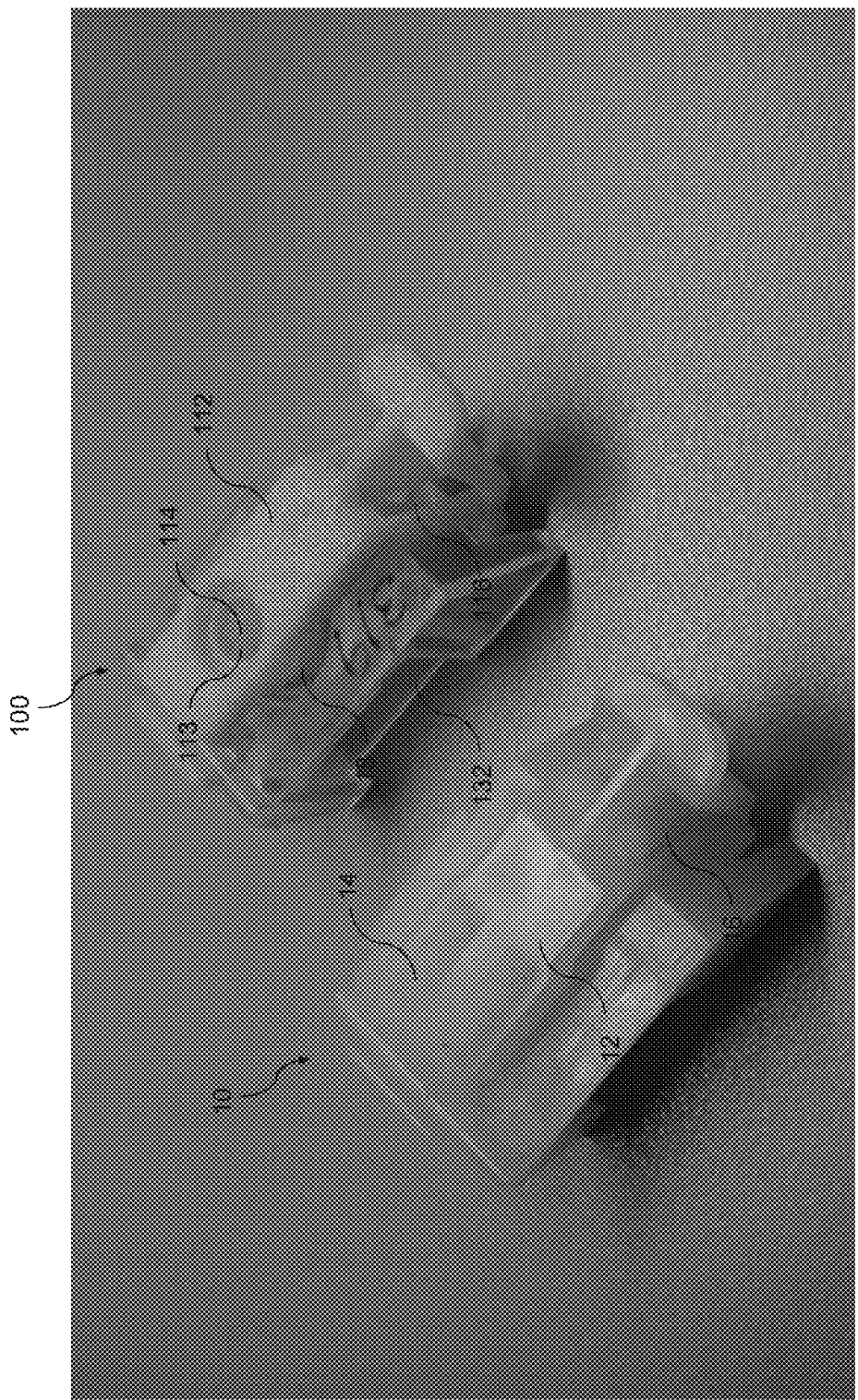
FIG. 10 illustrates perspective views of biomaterial handling devices in accordance with embodiments of the invention.
Figure 11:
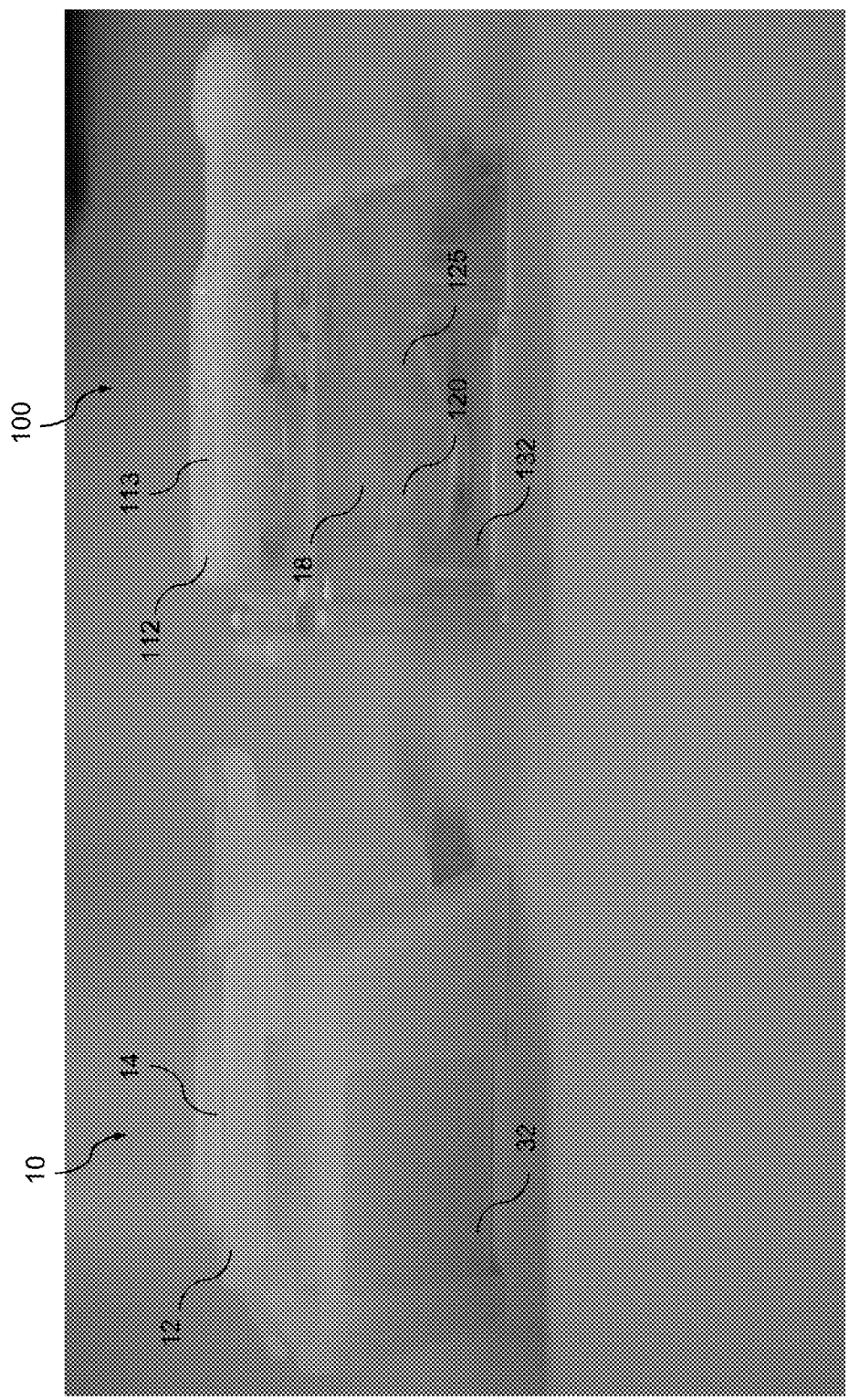
FIG. 11 illustrates side views of biomaterial handling devices of FIG. 10 in accordance with embodiments of the invention.

As demonstrated more clearly in FIGS. 10 and 11, the configuration in the top surface 119 of lid 112, however, is different than lid 12 of biomaterial handling device 10. Lid 112 of biomaterial handling device 100 includes an access port or hole 113. A membrane 114 may be disposed, for example, in a fixed fitted arrangement within access port or hole 113. Membrane 114 performs as a gas permeable moisture barrier seal effectively acting as a high $CO_2$ permeable and low water permeable barrier seal. Hence, the gas permeable moisture barrier seal of member 114 allows $CO_2$ exchange but limits evaporation. Examples of materials utilized as membrane 114 include silicone, rubber, low-density polyethylene (LDPE), polymethylpentene (PMP), polytetrafluoroethylene (PTFE), thermoplastic elastomer (TPE) and 4titude 4ti-0512 Gas Permeable Moisture Barrier Seal.

Membrane 114 may be affixed in any suitable manner within access port or hole 113. This may include, for example, heat sealing or adhesive securement of membrane 114 to the structure of the access port or hole 113. Disclosed embodiments of membrane 114 are preferably sterile and may be peelable and/or pierceable. Membrane 114 may be sufficient to have a seal integrity range of −20° C. to 80° C. including applications in Eukaryotic cell culture, bacterial culture, and long-term live cell assays. Permeability characteristics of the membrane 114 material may be as follows:
Water: approximately >1 gram/$m^2$d·bar
$O_2$: approximately 2900 $cm^3$/$m^2$d·bar
$CO_2$: approximately 4700 $cm^3$/$m^2$d·bar In an assembled configuration the attached hinged configuration 115 allows for rotational movement of lid 112, thereby permitting lid 112 to assume an open and closed position relative to main body portion 22. In a closed position, a flanged lip portion of lid 112 engages a locking portion of main body portion 122 in a snap-fitted arrangement, thereby locking lid 112 to main body portion 122 in a similar fashion as described with biomaterial handling device 10. Once lid 112 is locked into place against main body portion 122, membrane 114 abuts inlet port opening 29 of insert 18 to seal media within biomaterial handling device 100 such as in wash chamber 27 or waste chamber 24. At the same time seals 116 operate in a similar fashion as seals 16 (of biomaterial handling device 10), i.e., to seal respective openings along main body portion 122.

In an alternate arrangement of biomaterial handling device 100, membrane 114 may be omitted from access port or hole 113. In this arrangement, once media is inserted within wash chamber of 27 of insert 18, and lid 112 is affixed to main body portion 122 in a closed arrangement, a permeable moisture barrier seal may be applied directly to the top surface of the media through the access port or hole 113. For example, mineral oil may be applied to the top surface of the media to effectively act as the permeable moisture barrier seal. Thus, a high $CO_2$ permeable and low water permeable barrier seal is employed by depositing the same within access port or hole 113 of bio biomaterial handling device 100. The $CO_2$ permeable and low water permeable barrier seal may become self-sealant along edges 121 within access port or hole 113. In a disclosed embodiment, access port or hole 113 may include a ledge portion 123 disposed, for example, within an inner radius of the port or hole 113. Ledge portion 123 may accommodate overflow of the applied permeable moisture barrier seal, for example, disposed within access port or hole 113 and facilitate sealing of the permeable moisture barrier seal along surfaces and edges of ledge portion 123. In this manner, any overflow of the applied permeable moisture barrier seal is contained within port or hole 113 along surfaces and edges of ledge portion 123. Other examples of permeable moisture barrier seals may include materials such as agar and sodium alginate.

Thus, disclosed embodiments of the present invention provide distinct advantages over prior-art systems. Biomaterial handling device 10 provides a single device for performing IVF procedures and washing techniques. In a first washing function, biomaterial handling device 10 of the present invention is fully capable of washing away dead sperm and cumulous cells from a biomaterial sample. In a second washing function, biomaterial handling device 10 of the present invention is also fully capable of providing a pathogen washing to reduce the pathogen load on embryos. This generally is enacted at a two-cell stage and requires more media than in the first washing function. In addition, disclosed embodiments provide a sealing function of biomaterial handling device 10 for decontaminating the exterior of the device while effectively sealing and protecting biomaterials disposed therein. Conventional IVF systems fail to provide each of the distinctive functions as disclosed herein in one system. Embodiments of the present invention provide more accurate results for performing IVF procedures and washing techniques while reducing manual labor steps and potential for errors. Doing so provides more cost-effective treatments and solutions in the development of IVF and washing techniques.

Having described the many embodiments of the present invention in detail, it will be apparent that modifications and variations are possible without departing from the spirit and scope of the invention. Furthermore, it should be appreciated that all examples in the present disclosure, while illustrating many embodiments of the invention, are provided as non-limiting examples and are, therefore, not to be taken as limiting the various aspects so illustrated.

Figure 7:
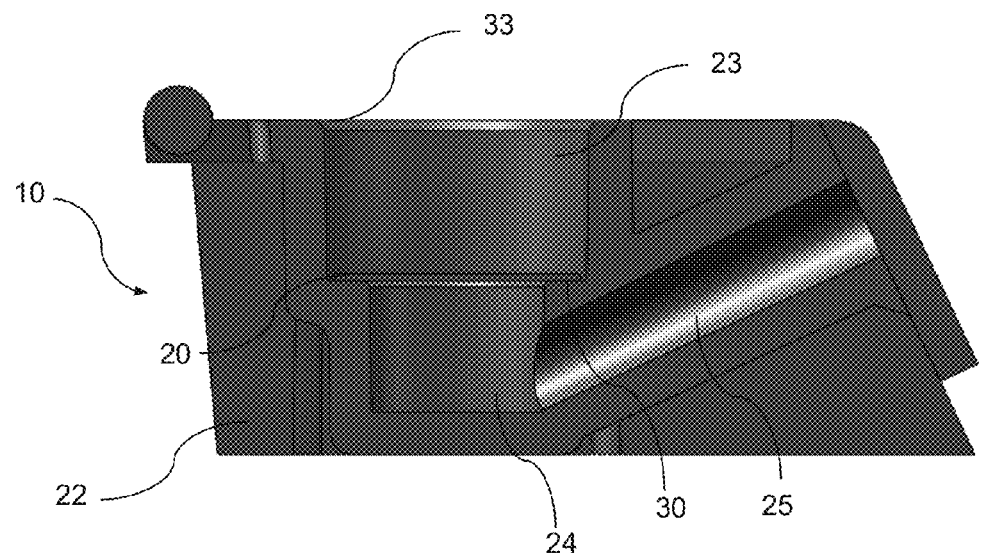
FIG. 7 illustrates an alternate embodiment of the biomaterial handling device of FIG. 1.

For example, turning to FIG. 7, while insert 18 facilitates sealing internal receptacle 23 and managing a pipette in assembly with biomaterial handling device 10, biomaterial handling device 10 may be utilized at a minimum with main body portion 22 in conjunction with filter 20. In the disclosed embodiment, main body portion 22 is configured to receive filter 20 within its cavity through opening 33 of internal receptacle 23. Thus, insert 18 is preferably positioned within the cavity of internal receptacle 23 and seated therein. Filter 20 may be disposed at an opening between internal receptacle 23 and waste chamber 24. In one disclosed configuration, the diameter of waste chamber 24 is smaller than the diameter of internal receptacle 23. In an assembled arrangement, the increased diameter of the internal receptacle 23 provides a flanged area 30 upon which filter 20 is seated on top thereof. In select embodiments, filter 20 may be physically attached at the opening from internal receptacle 23 to waste chamber 24. For example, filter 20 may be ultrasonically welded to the flanged area. In an alternative embodiment, filter 20 may be thermally welded to the flanged area.

Alternatively, in other disclosed embodiments, filter 20 may be fabricated as part of insert 18, for example, as part of a unitary assembly. Even still, additional embodiments may provide insert 18, filter 20 and main body portion 22 fabricated as a one piece assembly. While seals 14, 16, 116, and 117 have been described having certain characteristics and shapes, such description is not to be regarded as limiting the characteristics and shapes of the respective seals. Other characteristics and shapes may be employed sufficient to accommodate and effectively seal the inlet port opening 29 and outlet port opening 26 including, for example, any varying dimensions thereof.

While the present invention has been disclosed with references to certain embodiments, numerous modifications, alterations and changes to the described embodiments are possible without departing from the spirit and scope of the present invention, as defined in the appended claims. Accordingly, it is intended that the present invention not be limited to the described embodiments, but that it have the full scope defined by the language of the following claims and equivalents thereof.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless such changes and modifications depart therefrom.

What is claimed is:

1. A biomaterial handling device comprising:
   a main body portion comprising:
   an internal receptacle;
   a waste chamber connected to the internal receptacle, the waste chamber having a bottom surface having a plane;
   at least one output port connected to the waste chamber at one end and terminating at an output port opening at another end on a surface of the main body portion; and
   an insert having an inlet port opening at one end of the insert, wherein the inlet port opening has a plane and a wash chamber disposed within an interior of the insert,
   wherein the inlet port opening allows access to the wash chamber,
   wherein the wash chamber terminates into an opening at a bottom end of the insert,
   wherein the insert is disposed within the internal receptacle, wherein a longitudinal axis of the output port is configured at an acute angle from the plane of the bottom surface of the waste chamber.

2. The device of claim 1, wherein the insert comprises a sealing ring around an exterior circumference of the insert, wherein the internal receptacle is sealed by the sealing ring.

3. The device of claim 1, further comprising:
a removably attached lid connected to the main body portion for sealing the inlet port opening and the output port opening.

4. The device of claim 3, wherein the lid includes separate seals for sealing the inlet port opening and the output port opening, respectively.

5. The device of claim 4, wherein the seals comprise a material made from one of a thermoplastic elastomer and silicon.

6. The device of claim 4, wherein one of the seals is a gas permeable moisture barrier.

7. The device of claim 6, wherein the gas permeable moisture barrier is a membrane disposed in the lid.

8. The device of claim 7, wherein the membrane is fixed to the lid.

9. The device of claim 6, wherein the lid comprises an access port and the gas permeable moisture barrier is applied through the access port and over the inlet port opening.

10. The device of claim 9, wherein the gas permeable moisture barrier is mineral oil.

11. The device of claim 9, wherein the gas permeable moisture barrier forms a seal along edges of the access port.

12. The device of claim 9, wherein the access port accommodates overflow of the gas permeable moisture barrier.

13. The device of claim 6, wherein the gas permeable moisture barrier includes a high $CO_2$ permeable low water permeable material.

14. The device of claim 6, wherein the gas permeable moisture barrier includes one of polymethylpentene (PMP), silicone and low density polyethylene (LDPE).

15. The device of claim 3, wherein the lid is pivotably attached to the main body portion.

16. The device of claim 15, wherein the main body portion comprises a locking portion and the lid comprises a flanged lip portion, wherein when closed, the flanged lip portion engages the locking portion of the main body portion in a snap-fitted arrangement to lock the lid to the main body portion.

17. The device of claim 3, wherein the lid comprises a material made from one of polystyrene, polypropylene, and hi-density polyethylene.

18. The device of claim 1, wherein the output port extends from the waste chamber such that the output port opening is fixed at a height between the inlet port opening and the connection of the waste chamber to the internal receptacle.

19. The device of claim 18, wherein a level of media introduced into the wash chamber is maintained at a media volume within the wash chamber to never fall below the level of the wash chamber.

20. The device of claim 1, wherein the main body portion comprises:
a gas permeable moisture barrier.

21. The device of claim 20, wherein the gas permeable moisture barrier includes a high $CO_2$ permeability low water permeability material.

22. The device of claim 20, wherein the gas permeable moisture barrier includes one of polymethylpentene (PMP), silicone and low density polyethylene (LDPE).

23. The device of claim 1, wherein the insert and the main body portion comprise a material made from polystyrene.

24. The device of claim 1, wherein the inlet port opening is generally oval in shape.

25. The device of claim 1, further comprising a filter disposed at a bottom end of the insert, wherein the insert and filter are disposed within the internal receptacle.

26. The device of claim 25, wherein the filter is attached to the insert by one of an ultrasonic weld or a thermal weld.

27. The device of claim 25, wherein the filter comprises a mesh filter.

28. The device of claim 27, wherein the mesh filter comprises a hole size in a range from approximately 30-500 microns.

29. The device of claim 27, wherein the mesh filter comprises a material made from one of polyester, nylon, polystyrene, glass, high-density polyethylene (HDPE), polypropylene, and paper.

30. The device of claim 1, further comprising a slot configured into one side of the main body portion and a key configured on an opposite side of the main body portion, wherein the key of one device attaches to the slot of another device.

31. The device of claim 30, wherein multiple devices are attached to one another via respective keys and slots of the multiple devices to form an array of devices.

32. The device of claim 30, wherein the slot comprises a female member and the key comprises a male member, wherein the male member is sized to correspond to attach to the female member in a secure fashion.

33. The device of claim 32, wherein the female member and the male member are removably attached.

34. The device of claim 32, wherein the female member and the male member are attached via interference fit arrangement.

35. The device of claim 32, wherein the female member and the male member are attached via a snap-fit arrangement.

36. The device of claim 32, wherein the female member comprises a slot configuration and the male member is attached to the female member by sliding into the slot configuration.

37. The device of claim 32, wherein the female member comprises a key slot and the male member comprises a protrusion.

38. A biomaterial handling device comprising:
a main body portion comprising:
an internal receptacle;
a waste chamber connected to the internal receptacle, the waste chamber having a bottom surface having a plane;
at least one output port connected to the waste chamber at one end and terminating at an output port opening at another end on a surface of the main body portion; and
an insert having an inlet port opening at one end of the insert, wherein the inlet port opening has a plane and a wash chamber disposed within an interior of the insert,
wherein the inlet port opening allows access to the wash chamber,
wherein the wash chamber terminates into an opening at a bottom end of the insert,
wherein the insert is disposed within the internal receptacle, wherein the inlet port opening plane and the output port opening plane are at an oblique angle relative to each other.

39. The device of claim 38 further comprising:
a removably attached lid connected to the main body portion for sealing the inlet port opening and the output port.

40. The device of claim 39, wherein the lid includes separate seals for sealing the inlet port opening and the output port opening, respectively.

41. The device of claim 40, wherein the seals comprise a material made from one of a thermoplastic elastomer and silicon.

42. The device of claim 40, wherein the one of the respective seals is a gas permeable moisture barrier.

43. The device of claim 42, wherein the gas permeable moisture barrier is a membrane disposed in the lid.

44. The device of claim 43, wherein the membrane is fixed to the lid.

45. The device of claim 42, wherein the lid comprises an access port and the gas permeable moisture barrier is applied through the access port and over the inlet port opening.

46. The device of claim 45, wherein the gas permeable moisture barrier is mineral oil.

47. The device of claim 45, wherein the gas permeable moisture barrier forms a seal along edges of the access port.

48. The device of claim 45, wherein the access port accommodates overflow of the gas permeable moisture barrier.

49. The device of claim 42, wherein the gas permeable moisture barrier includes a high $CO_2$ permeable low water permeable material.

50. The device of claim 42, wherein the gas permeable moisture barrier includes one of polymethylpentene (PMP), silicone and low density polyethylene (LDPE).

51. The device of claim 39, wherein the lid is pivotably attached to the main body portion.

52. The device of claim 51, wherein the main body portion comprises a locking portion and the lid comprises a flanged lip portion, wherein when, closed the flanged lip portion engages the locking portion of the main body portion in a snap-fitted arrangement to lock the lid to the main body portion.

53. The device of claim 38,
wherein the output port extends from the waste chamber such that the output port opening is fixed at a height between the inlet port opening and the connection of the waste chamber to the internal receptacle.

54. The device of claim 38, further comprising a slot configured into one side of the main body portion and a key configured on an opposite side of the main body portion, wherein the key of one device attaches to the slot of another device.

55. The device of claim 54, wherein multiple devices are attached to one another via respective keys and slots of the multiple devices to form an array of devices.

56. The device of claim 54, wherein the slot comprises a female member and the key comprises a male member, wherein the male member is sized to correspond to attach to the female member in a secure fashion.

57. The device of claim 56, wherein the female member and the male member are removably attached.

58. The device of claim 56, wherein the female member and the male member are attached via interference fit arrangement.

59. The device of claim 56, wherein the female member and the male member are attached via a snap-fit arrangement.

60. The device of claim 56, wherein the female member comprises a slot configuration and the male member is attached to the female member by sliding into the slot configuration.

61. The device of claim 56, wherein the female member comprises a key slot and the male member comprises a protrusion.

* * * * *